US009259733B2

(12) United States Patent
Tuccelli et al.

(10) Patent No.: US 9,259,733 B2
(45) Date of Patent: Feb. 16, 2016

(54) DEVICE FOR A BIOLOGICAL LIQUID TREATMENT INSTALLATION

(71) Applicant: EMD Millipore Corporation, Billerica, MA (US)

(72) Inventors: Ronald Tuccelli, Winchester, MA (US); Sebastien Cirou, Schiltigheim (FR); Virginie Buisson, Neuvecelle (FR); Christine Abouayad El Idrissi, Eschau (FR); Jim Kelly, Melrose, MA (US)

(73) Assignee: EMD Millipore Corporation, Billerica, MA (US)

( * ) Notice: Subject to any disclaimer, the term of this patent is extended or adjusted under 35 U.S.C. 154(b) by 0 days.

(21) Appl. No.: 14/413,555

(22) PCT Filed: Jul. 18, 2013

(86) PCT No.: PCT/IB2013/055926
§ 371 (c)(1),
(2) Date: Jan. 8, 2015

(87) PCT Pub. No.: WO2014/016743
PCT Pub. Date: Jan. 30, 2014

(65) Prior Publication Data
US 2015/0190809 A1 Jul. 9, 2015

(30) Foreign Application Priority Data

Jul. 23, 2012 (FR) ...................................... 12 57131

(51) Int. Cl.
*B01D 61/30* (2006.01)
*B01L 3/00* (2006.01)
(Continued)

(52) U.S. Cl.
CPC .................. *B01L 3/561* (2013.01); *B01L 3/565* (2013.01); *C12M 47/12* (2013.01);
(Continued)

(58) Field of Classification Search
CPC ........ B01D 15/08; B01D 61/28; B01D 61/30; B01D 65/00; B01D 2311/2688; B01D 2313/06; B01D 2313/08; B30B 9/00; B30B 9/02; B30B 9/22; B30B 15/30; B30B 15/32; B01L 3/00; B01L 3/50; B01L 3/56; B01L 3/561; B01L 3/565; B01L 2200/0689; B01L 2300/0816; B01L 2300/0861; B01L 2300/0887; B01L 2300/123; B01L 2400/0655; C12N 1/02; C12N 1/04; C12N 1/34; C12M 1/00; C12M 1/12; C12M 23/00; C12M 23/02; C12M 23/04; C12M 1/007; C12M 1/126; C12M 1/14; C12M 1/34; C12M 21/00; C12M 23/14; C12M 23/16; C12M 23/26; C12M 47/12
USPC ......... 210/85, 90, 96.1, 134, 232, 241, 198.2, 210/321.6, 541, 542, 646; 137/343, 377, 137/571; 435/287.1, 289.1, 307.1, 308.1; 422/527, 537, 70, 544, 547, 555, 565; 220/200, 241, 242, 243, 244, 810, 845, 220/660, 661
See application file for complete search history.

(56) References Cited

U.S. PATENT DOCUMENTS 6,818,185 B1 * 11/2004 Petersen et al. ............... 422/547
8,499,794 B2 * 8/2013 Takahashi et al. ............ 137/829
(Continued)

FOREIGN PATENT DOCUMENTS

FR      2960796 A1    12/2011
FR      2961711 A1    12/2011
(Continued)

OTHER PUBLICATIONS

International Search Report and Written Opinion mailed Nov. 8, 2013 in corresponding PCT application No. PCT/IB2013/055926.
(Continued)

*Primary Examiner* — Joseph Drodge
(74) *Attorney, Agent, or Firm* — Nields, Lemack & Frame, LLC

(57) ABSTRACT

The invention concerns a device comprising a circuit comprising a bag (10) comprising two flexible films (65, 66), a press (9) comprising a first shell (16) disposed upright on a front face of a base of the device and a second shell (17) mounted on said first shell, which shells clamp said bag to form conduits (13); said press is provided with a system (170) for jamming at the location of a treatment zone (67) of the bag, which comprises a jamming member (171) provided with at least one jamming nipple (173) and a complementary jamming member (172) provided with a jamming channel (174) configured to receive said nipple; said jamming member (171) and complementary jamming member (172) and said bag (10) being configured in order for the latter to have a portion (175) in said treatment zone in which said films are jammed between said nipple and said channel.

30 Claims, 6 Drawing Sheets

(51) Int. Cl.
*C12M 1/12* (2006.01)
*C12M 1/00* (2006.01)

(52) U.S. Cl.
CPC . *B01L 2200/0689* (2013.01); *B01L 2300/0816* (2013.01); *B01L 2300/0887* (2013.01); *B01L 2300/123* (2013.01); *B01L 2400/0655* (2013.01); *Y10T 137/9029* (2015.04)

(56) References Cited

U.S. PATENT DOCUMENTS

| | | | |
|---|---|---|---|
| 2009/0011179 A1* | 1/2009 | Kikuchi et al. | 428/116 |
| 2009/0042293 A1* | 2/2009 | Hata et al. | 435/383 |
| 2010/0187167 A1* | 7/2010 | Reinbigler et al. | 210/85 |
| 2011/0315611 A1* | 12/2011 | Fulkerson et al. | 210/96.2 |
| 2012/0053520 A1 | 3/2012 | Kirkpatrick | |
| 2012/0138173 A1* | 6/2012 | Cirou et al. | 137/561 R |
| 2012/0138522 A1* | 6/2012 | Cirou et al. | 210/232 |
| 2012/0145616 A1* | 6/2012 | Weissenbach et al. | 210/198.2 |
| 2012/0284991 A1* | 11/2012 | Kusz et al. | 29/428 |
| 2013/0292319 A1* | 11/2013 | Fulkerson et al. | 210/321.78 |
| 2014/0263062 A1* | 9/2014 | Updyke et al. | 210/646 |
| 2015/0083320 A1* | 3/2015 | Putnam | 156/285 |

FOREIGN PATENT DOCUMENTS

| | | |
|---|---|---|
| GB | 1434786 A | 5/1976 |
| WO | 93/03295 A1 | 2/1993 |
| WO | 94/05346 A1 | 3/1994 |
| WO | 2011/161609 A1 | 12/2011 |

OTHER PUBLICATIONS

International Preliminary Report on Patentability mailed Feb. 5, 2015 in corresponding PCT application No. PCT/IB2013/055926.

* cited by examiner

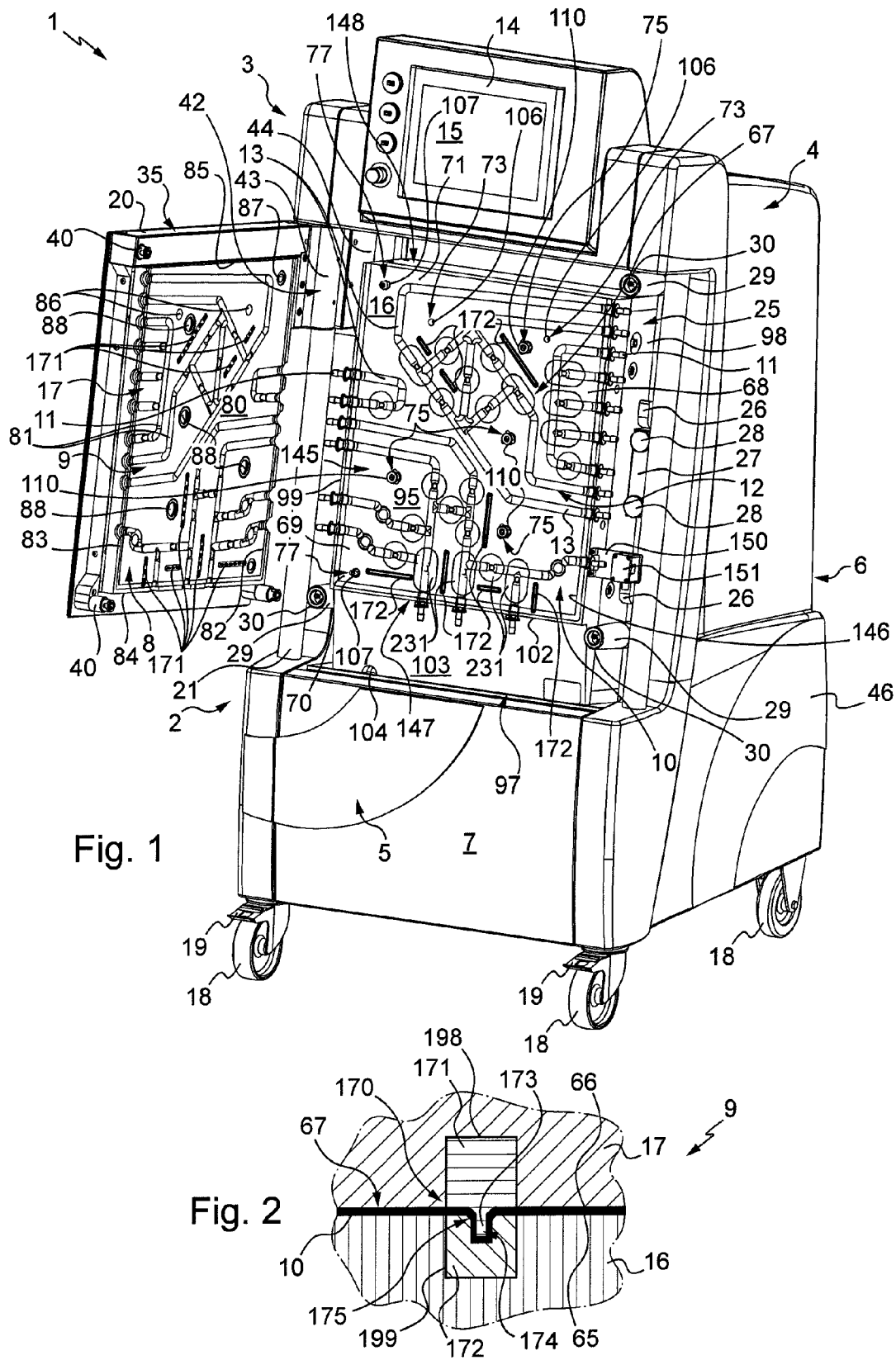

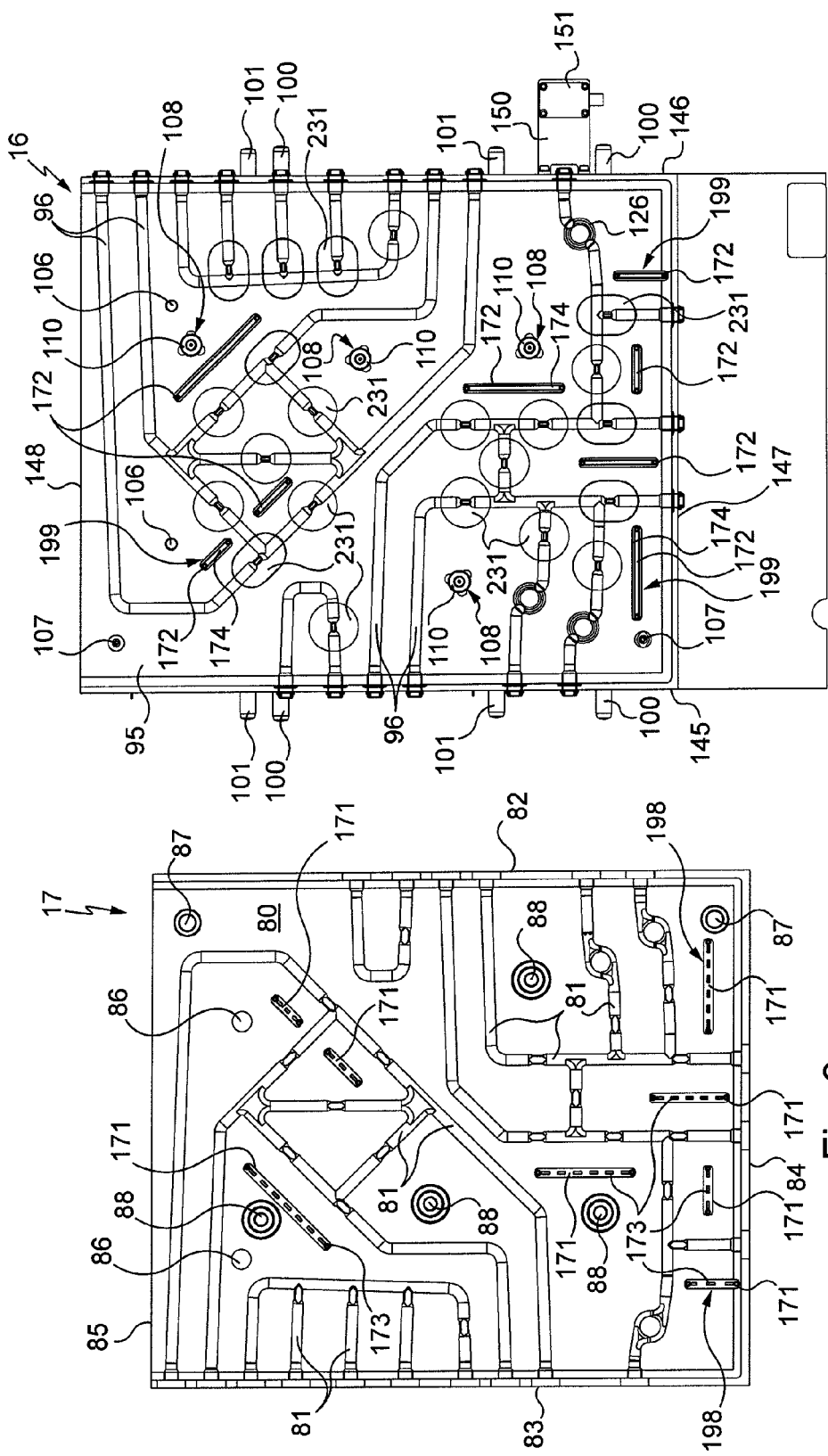

DEVICE FOR A BIOLOGICAL LIQUID TREATMENT INSTALLATION

The invention relates to a device for a biological liquid treatment installation, particularly but not exclusively, for purifying a biopharmaceutical liquid in order to obtain products such as monoclonal antibodies, vaccines or recombinant proteins.

It is known that biopharmaceutical liquids are in general obtained by culture in a bioreactor and that they must then be treated to achieve the required characteristics of purity, concentration, absence of viruses, etc.

The purification is carried out by means of a succession of treatments such as clarification, to eliminate the residues from the bioreactor culture, and viral filtration sometimes followed by diafiltration and concentration by tangential flow filtration (TFF). Other operations exist concerning purification, such as chromatography (XMO).

A number of types of container containing liquids can be connected to the inlet of the circuit, such as the source container that contains the product to be treated, but also the containers containing a cleaning liquid such as sodium hydroxide, a rinsing liquid such as pure water or a buffer liquid such as a saline solution. In addition to the container for collecting the treated liquid, various other containers for collecting cleaning, rinsing or buffer liquid, or for collecting residues, can be connected to the outlet of the circuit.

In a production context the liquid treatments can be carried out sequentially, the collecting container for the first treatment potentially becoming the source container for the next treatment, and so on until the last treatment is carried out.

These treatments are conventionally carried out in dedicated installations comprising stainless steel pipes and other parts such as tanks or filter housings, which necessitate operations before and after the actual treatment, which are relatively onerous, in particular operations of cleaning after use.

Within the last few years, these treatments have alternatively been carried out in installations in which the components in contact with the liquid are single-use components.

Such single-use components have the advantage of avoiding cleaning operations, but, to provide the required degree of security, the implementation of an installation with such components necessitates operations of selection, assembly and verification which are relatively complex.

This is especially the case when the number of pipes and other circuit components, for example connectors and pinch valves, is high and/or when the operating pressure is high.

From French patent application FR 2 960 796 there is known a device for a biological liquid treatment installation comprising a base having a front face, as well as a circuit.

The circuit comprises a plurality of connectors and a network for conveying liquid between said connectors, a bag comprising two flexible films and said conveying network connectors, as well as a press comprising a first shell and a second shell.

The first shell is disposed upright on the front face of the base and the second shell is mounted on the first shell.

The first shell and the second shell cooperate with the bag to form, between the flexible films, conduits of the routing network by clamping of the bag between the first shell and the second shell.

The two said flexible films of the bag are joined to each other and delimit a treatment zone for the liquid according to a closed outline, with the conveying network connectors emerging on the inside and on the outside on three sides of the outline.

The bag further comprises through apertures at the top of that bag for its positioning and the first shell comprises studs for hooking the bag on an upper part of the first shell, such that the hooking studs pass through the through apertures of the bag for suspending the bag.

Such devices are greatly appreciated since putting the bag in place (by suspension) on the first shell before the second shell is mounted on that first shell is particularly easy to carry out, with the bag then being clamped between the first shell and the second shell for the implementation of the biological liquid treatment in secure conditions of use.

The invention aims to provide a device enabling implementation of treatments for biological liquid that are even more secure while being simple, convenient and economical.

For this, the invention concerns a device for a biological liquid treatment installation comprising a base having a front face, and a circuit comprising a plurality of connectors and a network for conveying liquid between said connectors, which circuit comprises a bag comprising two flexible films and said conveying network connectors, which circuit further comprises a press comprising a first shell disposed upright on said front face of said base and a second shell mounted on said first shell, said first shell and second shell cooperating with said bag to form, between said flexible films, by clamping of said bag between said first shell and said second shell, conduits of said conveying network; the two said flexible films of said bag being joined to each other and delimiting a treatment zone for said liquid according to a closed outline, said conveying network connectors emerging on the inside and on the outside of at least one side of said outline;

characterized in that said press is provided with a system for jamming said bag at the location of said treatment zone thereof, said jamming system comprising at least one jamming member for jamming said bag and at least one complementary jamming member for jamming said bag, said at least one jamming member being provided with at least one jamming nipple and said at least one complementary jamming member being provided with at least one jamming channel configured to receive said at least one jamming nipple; said at least one jamming member, said at least one complementary jamming member and said bag being configured in order for the latter to have at least one portion in said treatment zone in which said films are jammed between said at least one jamming nipple and said at least one jamming channel.

By virtue of the invention, the bag is not only positioned in the press but it is furthermore fixed in position within that press, by an operation of jamming one or more portions of the treatment zone of that bag, which operation is implemented by a jamming system of the press.

More particularly, there are one or more jamming nipples and jamming channels, respectively formed on jamming members and complementary jamming members, which come to jam the films of the bag at the location of those portions of the treatment zone when the jamming nipples are received in the (complementary) channels. In such a state of jamming of the bag, the films are almost tangled between the jamming nipples and the jamming channels.

The jamming system of the device according to the invention advantageously makes it possible to fix the position of the bag prior to the start of a treatment and not to allow the latter to move in course of treatment despite the high stresses experienced by that bag.

More particularly, it should be noted that the bag is subjected to high forces of pressure due to the flow of the biological liquid which passes through its conduits, to high compression forces due to the mechanical actions at the time of the treatment itself (for example the actuation of pinch valves directly on the films of the bag to open/close the conduits) and to high traction and/or thrust forces when connections are made between the connectors of the conveying network and parts in the vicinity. It is by advantageously taking into account all these stresses that the implantation in the press of the jamming members and complementary jamming members is carried out.

The device according to the invention thus simply, conveniently and economically provides particularly high comfort and security of use for the preparation and the implementation of a treatment for biological liquid.

According to particularly simple, convenient and economical features of the device according to the invention:

- said at least one jamming member is fastened in a first recessed accommodation of said first shell and said at least one complementary jamming member is fastened in a second recessed accommodation of said second shell;
- said at least one jamming member is of parallelepiped general shape provided with a front wall from which projects said at least one jamming nipple;
- said at least one complementary jamming member is of parallelepiped general shape provided with a main opening in which is provided said at least one jamming channel.
- said at least one jamming nipple has a flared base and a straight wall remote from said flared base, and said at least one jamming channel has a back wall and flared edges.
- said at least one jamming member and said at least one complementary jamming member are disposed facing said treatment zone and in immediate proximity to a plurality of conduits of said routing network;
- said at least one jamming member and said at least one complementary jamming member are each disposed in a similar position to that of said first shell on said front face of said base, that is to say substantially vertical, or in a position perpendicular to that of said first shell on said front face, that is to say substantially horizontal, or in an intermediate position, that is to say inclined;
- said at least one jamming member is provided with a plurality of jamming nipples distributed longitudinally, regularly or irregularly, on a front wall of said at least one jamming member;
- said at least one complementary jamming member is provided with a single jamming channel formed longitudinally in a main opening of said at least one complementary jamming member;
- said bag comprises first through apertures on one side of said bag for its positioning, and said first shell comprises studs for hooking said bag to an upper part of said first shell, said hooking studs being configured to pass through said first through apertures of said bag.
- said second shell has a first hole, said bag comprises at least one second through aperture in said treatment zone and said device comprises a press locking system configured such that it locks said first shell and second shell together, which system is provided with at least one ball-lock pin having an unlocked state and a locked state, said ball-lock pin being fastened to said first shell, being configured to pass through said first shell and said second through aperture and to emerge in said first hole of said second shell, where said ball-lock pin is furthermore configured to be free therein in said unlocked state and to be fastened therein in said locked state; and/or
- said bag comprises at least one third through aperture on one side of said bag, said first shell comprises at least one dowel pin configured to pass through said third through aperture, and said second shell comprises at least one second hole configured to receive said dowel pin of said first shell;

According to particularly simple, convenient and economical features of the device according to the invention, the latter comprises a movable or removable door, said device having a closed door position, in which second shell is disposed in said door to form said circuit, and which furthermore has a position, other than said closed door position, in which said bag is carried only by the first shell.

The device according to the invention is thus provided with a base and a single door for carrying out different types of treatments, by virtue of a modular circuit of which the modules (first shell, second shell and bag) are interchangeable depending on the treatments carried out.

It is to be noted that it is also possible to unjam then change the bag very simply and very rapidly and if necessary the first shell and the second shell so as to perform a new treatment, whether of the same type or a different type.

To be precise, for this it suffices to actuate the passage from the closed door position to the other position, that is to say to open or remove the door from the device, so as to unjam the portions of the treatment zone of the bag that are jammed between the jamming nipples and the jamming channels of the jamming system, to then be able to remove that bag. This may be carried out prior to or after having disconnected pipes leading from treatment members in the vicinity and that were connected beforehand to connectors emerging from the bag, then if necessary to remove the first and second shells respectively from the base and from the door. Lastly, it suffices to install in the device first and second shells as well as a bag for the second treatment, to actuate the passage from the other position to the closed door position so as to position and fix the new bag between the first and second shells, by jamming portions of the treatment zone of the bag between the jamming nipples and the jamming channels of the jamming system, then to connect pipes to the connectors emerging from the bag.

Where the door is moveable relative to the base, it suffices first of all to open it then close it again on the base.

Where the door is removable, it suffices first of all to remove it then to put it back on the base.

In this way, it is possible to pass from a first treatment, for example by chromatography, to a second treatment of another type, for example by tangential filtration, in a simple, economical, convenient and secure manner.

Of course, where the following treatment is different from the previous one, the first and second shells as well as the bag for the second treatment have features (conduits of the conveying network, connectors) that are different from the first and second shells as well from the bag from the previous treatment, so as to form a circuit having an architecture adapted to the following treatment.

Furthermore, in addition to the device according to the invention, the biological liquid treatment installation comprises, depending on the treatments carried out, one or more other devices, for example juxtaposed to the device according to the invention.

This or these other device or devices is or are provided with the treatment components in the vicinity mentioned above formed in particular by one or more pumps, for example of the diaphragm type, and/or by a source container containing the product to treat and/or by a treated liquid collecting container and/or by a chromatography column, these treatment components in the vicinity each being connected to the bag, directly or not.

According to other particularly convenient preferred features, said device comprises a hinge system hinging said door relative to said base, said hinge system being disposed only on one side of said door so as to form, in the closed door position, lateral clearances between said door and said base over the rest of a perimeter of said door, so as to enable free access to the connectors of said bag.

By virtue of the arrangement of the hinge system enabling the hinging of the door relative to the base, lateral clearances are advantageously formed over a major part of the outer perimeter of the door, between that door and the base.

Thus, the bag may comprise connectors emerging to the exterior of a major part of its outline with free access thereto by virtue of the lateral clearances, to connect pipes thereto coming from the treatment components in the vicinity (pump (s) and/or container(s) and/or column).

Furthermore, as the door is connected to the base only on one side, for example on the top of the door, the mounting and the jamming of the bag on the first shell is greatly facilitated.

More particularly, it is possible to connect the bag to the treatment components surrounding it before disposing it on the first shell, without then being hindered by the hinge, that is to say at the time of disposing the bag on the first shell, even though it is already connected to pipes.

Moreover, by virtue of the lateral clearances formed, the routing of the pipes which connect the bag to the treatment components in the vicinity is simplified, while avoiding the pipes passing in front of the door.

According to other particularly convenient preferred features of the device according to the invention, said circuit comprises instruments necessary for the treatment of said biological liquid, in particular valves to allow or prevent the passage of said liquid in said conduits, and/or sensors of physico-chemical values of said liquid, and said instruments are integrated into said first shell.

The disclosure of the invention will now be continued with the description of an embodiment, given below by way of illustrative and non-limiting example, with reference to the accompanying drawings, in which:

FIG. 1 is a perspective view of a device for a biological liquid treatment installation, in accordance with the invention, in which a press of the device is in an open state and a bag suspended;

FIG. 2 is a detail view of the device of FIG. 1, in which the press is in a closed state and the bag jammed in the press;

FIGS. 3 and 4 are respectively front views of a second shell and of a first shell of the device of FIG. 1, without the bag;

Figure 5:
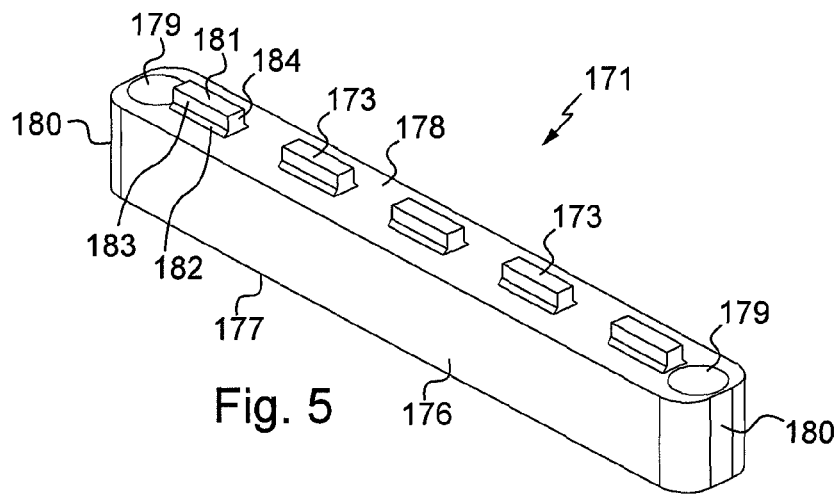
FIGS. 5 to 8 are views from different angles of a jamming member of a jamming system of the device of FIG. 1.

FIG. 1 illustrates a device 1 for the installation for biological liquid treatment by chromatography. Treatments by chromatography are known and it should be noted that French patent application 2 961 711 describes the steps of implementation of such a treatment, with furthermore a liquid routing network similar to that shown in FIGS. 1, 3 and 4.

The device 1 is of generally parallelepiped form.

This device 1 comprises a base 2 having a first lateral face 3, a second lateral face 4 which is an opposite face to the first lateral face 3, a front face 5 meeting the first and second lateral faces 3 and 4, and a back face 6 which is an opposite face to the front face 5 and which meets the first and second lateral faces 3 and 4.

The device 1 further comprises a circuit 8 provided with a press 9 and a bag 10, which comprises a plurality of connectors 11 for liquid and a network 12 for conveying liquid between those connectors 11 including conduits 13 configured in a treatment zone 67 of that bag 10.

The press 9 comprises two shells 16 and 17 each formed from a solid block of rigid material. Here, the shells 16 and 17 are of polyoxymethylene (POM), also called acetal, and each has a generally parallelepiped form.

The press 9 further comprises a jamming system 170 (FIG. 2) of the bag 10 provided with a plurality of jamming members 171 of the bag 10, also called male inserts, and complementary jamming members 172 of the bag 10, also called female inserts, described below in more detail.

It should be noted that in FIG. 1, the bag 10 is mounted on the shell 16 and that for reasons of clarity, the members visible on shell 16 but covered by the bag 10 are visible here thanks to transparency (through the bag 10) and are represented in continuous line. In reality, despite the transparency of the bag 10 (described in more detail below), some parts should appear at least slightly faded.

The shell 16 is mounted on the front face 5 of the base 2.

The device 1 further comprises a door 20 hinged to the base 2 and the shell 17 is mounted in that door 20.

The device 1 has a closed door position in which the door 20 is closed and covers the shell 16 (the press is then closed, as is partially visible in FIG. 2), and another position in which the bag 10 is carried only by the shell 16 (the press is then open as visible in FIG. 1).

In this other position, the shell 17 is away from the shell 16.

In the closed door position, the bag 10 is inserted between the two shells 16 and 17.

The device 1 is provided, at the bottom, with a closed bay 46 intended to receive one or more tanks if necessary.

This bay 46 is closed by a sliding panel 7 disposed on the front face 5 of the device 1, which panel 7 is configured to be moved in translation downwardly then towards the back of the device 1 so as to insert and withdraw the tanks.

A control panel 14 is arranged at the top of the front face 5 of the device 1.

This control panel 14 is provided with a graphical touch interface 15 enabling the biological liquid treatment process to be verified and controlled.

This control panel 14 is thus arranged at a height enabling a user to make use of it.

In order to make it easier to move, the device 1 is in the form of a cart mounted on four castors 18 (of which three can be seen in FIG. 1), with two castors situated under the front face of the device 5 which comprise a brake 19, and with the device 1 furthermore having two handles 21 on respective opposite sides of the front face 5, in the vicinity of the respective lateral faces 3 and 4.

The device 1 comprises an inclined chassis 25 at its front face 5.

On each of its left and right sides, the chassis 25 comprises two superposed L-shaped hooking claws 26 emerging from the respective side and extending upwardly.

A support plate 27 is fastened to the right side of the chassis 25, between the two hooking claws 26.

This support plate 27 is disposed in the immediate vicinity under the hooking claw 26 situated higher on the right side, so as to leave free access to the hooking claw 26 situated lower down on that same right side.

The support plate 27 comprises two fastening heads 28 on which a platform (not shown) is configured to be fastened so as to dispose thereon instruments (not shown) 151 for the treatment of the biological liquid.

Such a platform is similar to the platform 150 visible just below that support plate 27, which comprises instruments 151 for the treatment of the biological liquid.

These instruments 151 may for example be optional kits such as sensors measuring pH or conductivity and are chosen by the user according to the type of treatment to carry out.

The base 2 of the device 1 further comprises devices 29 which, with complementary devices 40 of the door 20, enable the positioning and the locking of that door 20 in the closed door position.

There are three of the devices 29, which are situated at the corners of the chassis 25, respectively at top right, bottom right, and bottom left.

These devices 29 each comprise a body, an annular shoulder (not shown), a head connected to that annular shoulder, that head having the form of a conical tube and being provided internally with a rod 30 with a conical tip. The body comprises a pneumatic chamber, a piston that is mechanically linked to the rod 30 with a conical tip, which rod 30 is adapted to extend within the head.

The door 20 comprises a frame 35 having a generally rectangular outline.

The frame 35 comprises four sides and three complementary devices 40 adapted to cooperate with the devices 29 of the base 2, which complementary devices 40 are respectively situated at the upper left, bottom left, and bottom right corner.

These complementary devices 40 are provided with a first cylindrical portion and a second cylindrical portion that is hollow and connected to the first portion by a shoulder. This second portion is of smaller diameter than the diameter of the first portion. Furthermore, the second portion is provided with three apertures on the outer surface.

These complementary devices 40 further comprise three balls (not shown) each able to project from the second portion by passing through a respective aperture.

In the closed door position, each second portion of a respective complementary device 40 of the door 20 is inserted into a respective head of a respective device 29 of the base 2.

The devices 29 and complementary devices 40 form, in pairs, a ball-lock pin system provided with a pneumatic jack of double-acting type with a spring (not shown), having an extended position and a retracted position, and of which the operation is well-known.

The rod 30 of the device 29 is adapted to be introduced into the hollow second cylindrical portion when the jack is in its extended position.

In this position of the jack, the rod 30 pushes the balls until each of them passes through an aperture, so blocking movement of the door 20 relative to the base 2.

The device 1 further comprises a hinge system by virtue of which the door 20 is hinged to the base 2.

This hinge system is provided with a single hinge 42 comprising a first hinge portion 43 fastened to the top right corner of the frame 35 of the door 20, and a second hinge portion 44 fastened to the lateral face 3 of the base 2 of the device 1.

On the upper part of the second hinge portion 44 a mechanical spring (not shown) is arranged with a plastic stop to facilitate the opening and closing of the door 20.

The device also includes a position sensor (not shown) to verify and provide security for the opening and closing of the door 20, by detecting the closed door position and the other position.

A pneumatic system (not shown) is also arranged on the upper part of the second hinge portion 44 so as to supply a system (not shown) for locking the shell 17 and which is situated in the door 20.

In the closed door position, the rotational axis about which the first hinge portion 43 of the door 20 pivots is offset relative to a parting surface formed between the shells 16 and 17 when they clamp the bag 10 between them.

This axial offset towards the front of the device 1 enables lateral clearances to be formed between the door 20 and the base 2 at the outer perimeter of the door 20.

Thus, the access to the connectors 11 of the bag 10 is greatly facilitated.

As can be seen better in FIG. 3, the shell 17 has a reference surface 80, which is flat here, and a plurality of shaping channels 81 recessed into that reference surface 80. This shell 17 has a first side 82 and a second side 83 that is an opposite side to the first side 82, a third side 84 and a fourth side 85 that is an opposite side to the third side 84, these third and fourth sides 84 and 85 each meeting the first and second sides 82 and 83.

On its fourth side 85, the shell 17 is provided with two positioning holes 86 for positioning the bag 10 in suspension, which are arranged facing positioning apertures 73 of the bag 10 in the closed door position, with bag 10 clamped between the shells 16 and 17.

Furthermore, the shell 17 is provided with two other positioning holes 87 for positioning the door 20 in the closed door position, one of which is situated at the first side 82 of the shell 17, and the other at the other extreme, towards the bottom of the shell 17.

These two positioning holes 87 are arranged so as to face positioning apertures 77 of the bag 10 in the closed door position, with the bag 10 clamped between the shells 16 and 17.

In a central zone, the shell 17 further comprises four locking holes 88 of greater diameter than that of the positioning holes 86 and 87 of that shell 17, which locking holes 88 serve for the locking together of the shells 16 and 17.

These four locking holes 88 are situated at the locations where there are the most channels 81 serving for the formation of the conduits 13, since it is at these locations that the force of pressure is greatest during the treatment. The locking holes 88 are thus at least partially surrounded by channels 81.

These four locking holes 88 are arranged so as to face locking apertures 75 of the bag 10 in the closed door position, with the bag 10 clamped between the shells 16 and 17.

The shell 17 further comprises a plurality of recessed accommodations 198 (FIGS. 2 and 3) each formed in immediate proximity to several shaping channels 81 (at least two), and at the location of junctions between those channels 81.

These recessed accommodations 198 are here sited roughly at the center of the shell 17, between its first and second sides 82 and 83, and are distributed substantially over the entire height of that shell 17, between its third and fourth sides 84 and 85.

Each recessed accommodation 198 is of parallelepiped general shape with rounded contours and is provided to receive one of the jamming members 171, here called male insert, of the jamming system 170.

The male inserts 171 are here each disposed and fastened in a recessed accommodation 198 of the shell 17.

The male inserts 171 are each disposed facing a portion 175 of the treatment zone 67 and in immediate proximity to a plurality of shaping channels 81 and thus in immediate proximity to a plurality of conduits 13 of the routing network 12.

Some of the male inserts 171 are here disposed in a similar position to that of the shell 17 in the door 20, that is to say substantially vertical, other male inserts 171 are here disposed in a position perpendicular to that of the shell 17 in the door 20, that is to say substantially horizontal, and still other male inserts 171 are here disposed in an intermediate position, that is to say inclined.

Of course, like the recessed accommodations 198 of the shell 17, the male inserts 171 are here sited roughly at the center of the shell 17, between its first and second sides 82 and 83, and are distributed substantially over the entire height of that shell 17, between its third and fourth sides 84 and 85.

A male insert 171 will be described in more detail with reference to FIGS. 5 to 8.

The male inserts 171 each have a body 176 of parallelepiped general shape and provided with a front wall 178 from which projects a plurality of jamming nipples 173, here numbering five.

The body 176 is furthermore provided with a back wall 177 which is an opposite wall to the front wall 178, the back wall 177 being configured to come to bear against a back of the recessed accommodation 198.

The body 176 has two ends 180 which are opposite ends and at the location of each of which is formed an aperture 179 opening on respective opposite sides of the body 176, on the front wall 178 and on the back wall 177.

These apertures 179 enable the passage of fastening screws to fasten the male insert 171 in the recessed accommodation 198 of the shell 17.

The jamming nipples 173 are similar to each other here (in dimensions and shape) and are longitudinally distributed regularly over the front wall 178.

Each jamming nipple 173 has a flared base formed by two beveled longitudinal walls 182 which are each connected to the front wall 178, and by two straight longitudinal walls 183 which are each connected to a beveled longitudinal wall 182.

Each jamming nipple 173 furthermore has a straight wall 181 which is flat and remote from the flared base, and which connects the two straight longitudinal walls 183.

Each jamming nipple 173 furthermore has two straight lateral walls 184 connecting the longitudinal walls 182 and 183 forming the flared base.

Figure 6:
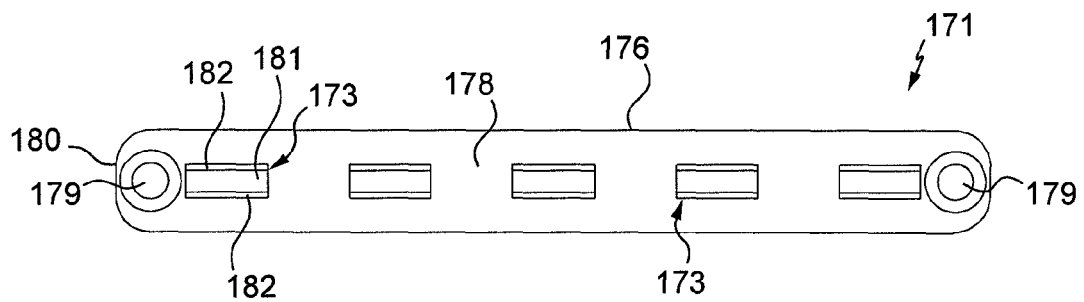
Figure 7:
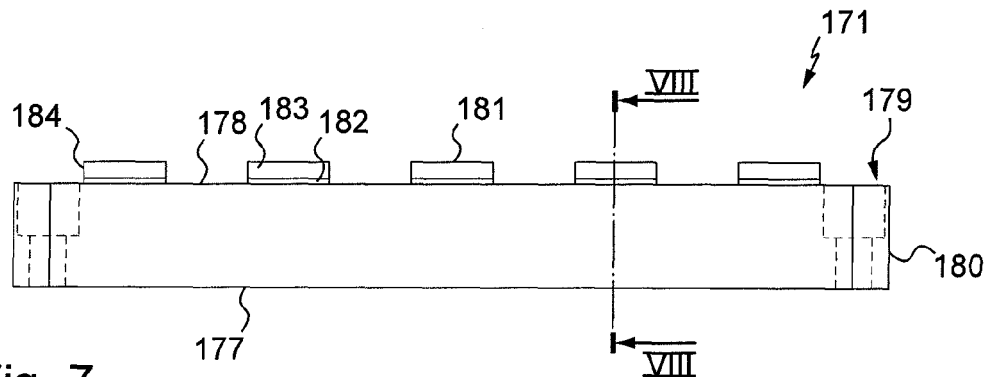
Figure 8:
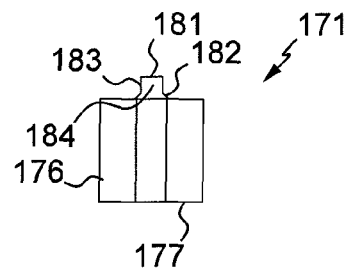
Figure 9:
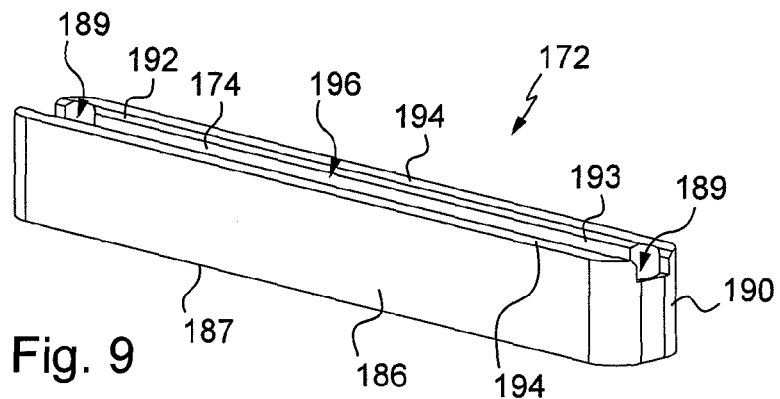
FIGS. 9 to 12 are views from different angles of a complementary jamming member of the jamming system of the device of FIG. 1.
Figure 10:
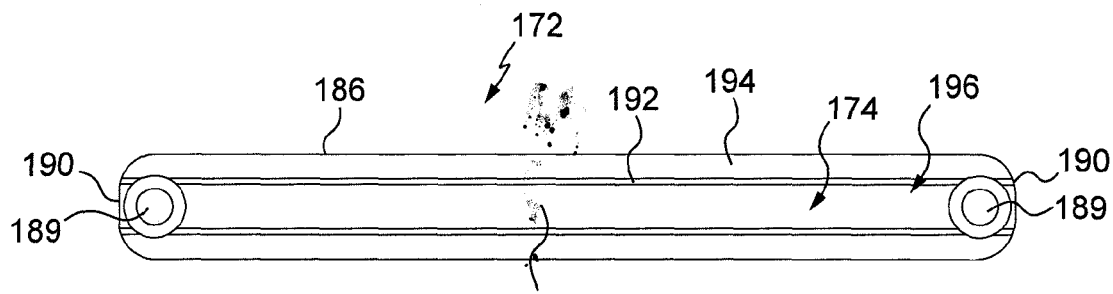
Figure 11:
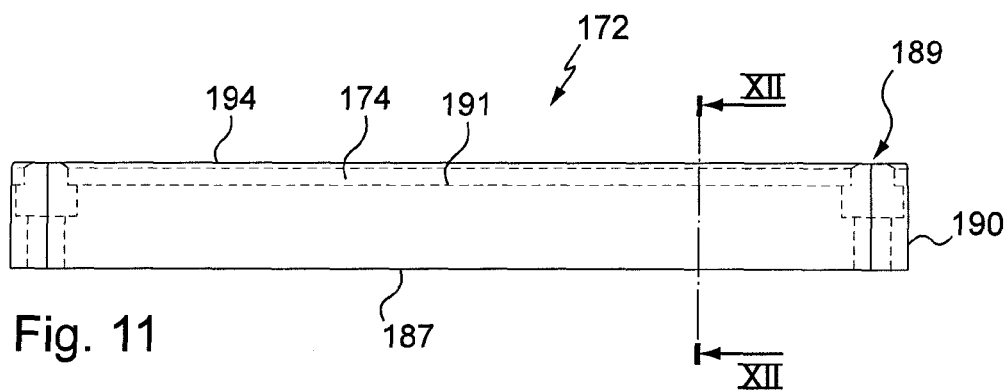
Figure 12:
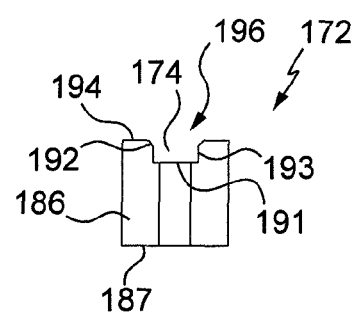

It will be noted that the five jamming nipples 173 are aligned on the front wall and interposed between the two apertures (FIG. 6).

As can be seen better in FIG. 4, the shell 16 has a flat reference surface 95 and shaping channels 96 recessed relative to the reference surface 95, each facing a corresponding shaping channel 81.

Generally, the surfaces 80 and 95 have similar dimensions and the arrangement of the shaping channels 96 is the mirror image of the set of the shaping channels 81.

It should be noted that the shaping channels 81 and 96 are of variable semi-elliptical cross-section.

The surfaces 80 and 95 may be applied against each other with the channels 81 and 96 in register with each other to delimit a network of cavities which are each generally tubular.

The shell 16 has a first side 145 and a second side 146 that is an opposite side to the first side 145, a third side 147 and a fourth side 148 that is an opposite side to the third side 147, which third and fourth sides 147 and 148 each meet the first and second sides 145 and 146.

The shell 16 furthermore has, on the opposite lateral walls 98 and 99, dowel pins 100 adapted to be engaged, by virtue of a vertical translational movement from top to bottom when the shell 16 is against the chassis 25, in the hooking claws 26 disposed on that chassis 25.

Furthermore, on those same opposite lateral walls 98 and 99, the shell 16 has rods 101 for manipulating the shell 16.

This manipulation is carried out by the user of the device 1, or with the help of a winch, which may for example be electric.

Thanks to the inclination and the weight of the shell 16, and thanks to the engagement of the dowel pins 100 in the hooking claws 26, the shell 16 is securely fastened to the chassis 25.

On its flat reference surface 95, the shell 16 furthermore has a re-entrant portion 102 which is extended downwardly by a slanting surface 103, the slant of which is directed inwardly of the device 1.

This slanting surface 103 enables the provision of access to the bay 46 comprising the containers.

On a lower face 97, the shell 16 further comprises a channel 104 of inverted gutter shape emerging on the slanting surface 103.

This channel 104 serves as a fool-proof device during the installation of the shell 16 on the chassis 25 of the base 2, in order for the reference surface 95 to be turned outwardly.

The shell 16 further comprises, on its fourth side 148, two aligned hooking or suspension studs 106 which are evenly spaced apart.

These studs 106 are configured to pass through the positioning apertures 73 of the bag 10 for the suspension of the latter on the shell 16.

Furthermore, the distal end of these same hooking studs 106 is adapted to be inserted into the positioning holes 86 of the shell 17 in the closed door position.

The shell 16 comprises two positioning dowel pins 107 for positioning the door 20, one of which is situated on the fourth side 148 of the shell 16 close to a hooking stud 106 situated at the top left of that shell 16, the other positioning dowel pin 107 being situated at the other extreme, that is to say at the bottom of the shell 16, between two shaping channels 96 at the location of the third side 147.

These positioning dowel pins 107 are adapted to pass through the apertures 77 of the bag 10, and the distal end of these positioning dowel pins 107 is adapted to be inserted into the positioning holes 87 of the shell 17.

The shell 16 further comprises four locking holes 108 (FIG. 4) which are situated at the locations where there are the most channels 96 serving for the formation of the conduits 13, since it is at these locations that the force of pressure is greatest during the treatment. The locking holes 108 are thus at least partially surrounded by channels 96.

These locking holes 108 are arranged so as to face the locking through-apertures 75 of the bag 10 when it is disposed on the shell 16, and also to face the corresponding locking holes 88 of the shell 17 in the closed door position.

The locking holes 108 of the shell 16 are passed through by the ball-lock pins 110 for the locking together of the shells 16 and 17 when the door 20 is in its closed position, and for the clamping of the bag 10 in the circuit 8.

Each ball-lock pin 110 comprises a body connected to the shell 16, and an annular shoulder provided with a transverse face and connected to a head (which are not shown). The body comprises a pneumatic chamber and a piston, the piston being mechanically connected to a rod with a conical tip (not shown). This rod extends in the head of the pin 110 and three balls (not shown) are arranged so as to be able to project from the head by passing through apertures formed in that head. The pin 110 is similar to a double-acting type jack and has an extended position and a retracted position.

The head of each pin 110 passes through the corresponding locking hole 108 of the shell 16, this head also passes through the corresponding locking aperture 75 of the bag, and this head lastly emerges into a corresponding locking hole 88 of the shell 17 in the closed door position.

When a first portion of the pneumatic chamber of the pin 110 is placed under pressure, the piston is acted upon. When the piston is at end of stroke, the balls are in extended position, that is to say that they project from the head to extend into the locking hole 88 of the shell 17.

The locking holes 88 are configured such that, when the balls 119 are extended, the shells 16 and 17 are securely locked.

When a second portion of the pneumatic chamber of the pin 110 is placed under pressure, this second portion being opposed to the first portion, the piston is urged towards the other end of stroke position. When that position is reached, the balls are in retracted position, that is to say they go back into the head.

In addition to the shells 16 and 17, the device 1 comprises instruments, here installed on the back of the shell 16, which are required for the treatment of the biological liquid illustrated in FIG. 3.

The shell 16 further comprises a plurality of recessed accommodations 199 (FIGS. 2 and 3) each formed in immediate proximity to several shaping channels 96 (at least two), and at the location of junctions between those channels 96.

These recessed accommodations 199 are here sited roughly at the center of the shell 16, between its first and second sides 145 and 146, and are distributed substantially over the entire height of that shell 16, between its third and fourth sides 147 and 148.

Each recessed accommodation 199 is of parallelepiped general shape with rounded contours and is provided to receive one of the complementary jamming members 172, here called female insert, of the jamming system 170.

The female inserts 172 are here each disposed and fastened in a recessed accommodation 199 of the shell 16.

The female inserts 172 are each disposed facing a portion 175 of the treatment zone 67 and in immediate proximity to a plurality of shaping channels 96 and thus in immediate proximity to a plurality of conduits 13 of said routing network 12.

Some of the female inserts 172 are here disposed in a similar position to that of said shell 16 on the front face 5 of the base 2, that is to say substantially vertical, other female inserts 172 are here disposed in a position perpendicular to that of the shell 16 on the front face 5, that is to say substantially horizontal, and still other female inserts 172 are here disposed in an intermediate position, that is to say inclined.

Of course, like the recessed accommodations 199 of the shell 16, the female inserts 172 are here sited roughly at the center of the shell 16, between its first and second sides 145 and 146, and are distributed substantially over the entire height of that shell 17, between its third and fourth sides 147 and 148.

A female insert 172 will be described in more detail with reference to FIGS. 9 to 12.

The female inserts 172 each have a body 186 of parallelepiped general shape and provided with a main opening 196 in which is formed a single jamming channel 174.

The body 186 is furthermore provided with a back wall 187 remote from the front opening 196, the back wall 187 being configured to come to bear against a back of the recessed accommodation 199.

The body 186 has two ends 190 which are opposite ends and at the location of each of which is formed an aperture 189 opening on respective opposite sides of the body 186, in the main opening 196 and on the back wall 187.

These apertures 189 enable the passage of fastening screws to fasten the female insert 172 in the recessed accommodation 199 of the shell 16.

The main opening 196 emerges at both ends 190.

The single jamming channel 174 is formed to receive the jamming nipples 173 of the facing male insert 171, as described below.

The single jamming channel 174 has a back wall 191 and flared edges on respective opposite sides of the single jamming channel 174.

These flared channels are here formed by two straight longitudinal walls 193 each connecting to the back wall 191, by two beveled longitudinal walls 192 each connecting to a respective straight longitudinal wall 193, and by two straight walls 194 forming a front face of the female insert 172.

The single jamming channel 174 extends longitudinally and is configured to face the five jamming nipples 173, with the same alignment as them.

The channel 174 is of complementary shape to the nipples 173, such that these latter are configured to fit inside the channel 174.

This is due to the fact that the back wall 191 of the channel 174 is configured to receive the straight walls 181 of the nipples 173, that the straight longitudinal walls 193 of the channel 174 are configured to face the straight longitudinal walls 183 of the nipples 173, that the beveled longitudinal walls 192 of the channel 174 are configured to receive, bearing upon them, the beveled longitudinal walls 182 of the nipples 173, and that the straight walls 194 of the female insert 172 are configured to receive, bearing upon them, the front wall 178 of the male insert 171.

The device 1 comprises a pneumatic distributor (not shown) and components for verification and control to perform various treatments of that liquid, which components are formed for example by a verification and command unit.

The device 1 further comprises pinch valves (not shown) provided with actuators (not shown) to pinch a corresponding conduit 13 so as to prevent or allow the passage of liquid in that conduit 13, and pressure sensors 126.

The actuators each comprise a body fastened to the shell 16 and a moveable pinching finger having a retracted position when the valve is in an open position, and an extended position when the valve is in a closed position.

The body comprises a pneumatic chamber, a piston and an accommodation provided with a spring accommodated in the shell, with the spring surrounding a rod linking the piston and the finger.

The pneumatic chamber, when it is under pressure, biases the piston against the spring. When the piston is at end of stroke, the finger is in retracted position. When the pneumatic chamber is at atmospheric pressure, the spring biases the piston towards the other position of end of stroke. When the latter is reached, the moveable finger is in extended position.

At its distal end, the moveable finger is generally shaped like the profile of the shaping channel 81 of the shell 17. In the extended position, the moveable finger projects into one of the channels 81.

The valve further comprises, in register with the moveable finger, an elastically compressible pad 231, which pad 231 forms part of an individual local plate of silicone molded in one piece. This pad 231 has a first face nearest the moveable finger and a second face nearest the conduit 13 to pinch. The second face of the pad 231 is concave and locally delimits the shaping channel 96 of the shell 16.

Each actuator enables a conduit 13 to be pinched between its moveable finger and shell 17, to allow or prevent the passage of the liquid at that location. To pinch the conduit 13, the valve passes from its open position in which the moveable finger is in a retracted position in which it does not pinch the conduit 13, to its closed position in which the moveable finger is in an extended position in which it pinches the conduit 13.

The finger, at the time it is extended, pushes the pad 231 towards the shaping channel 81 of the shell 17. Thus, the pad 231 passes from a resting configuration in which its second face is concave and locally delimits the shaping channel 96 of the shell 16 of the conduit 13 to pinch, to a pinching configuration in which its second face is convex, with the conduit 13 and the pad 231 sandwiched between the shaping channel 81 of the shell 17 of the conduit 13 to pinch and the moveable pinching finger.

It should be noted that the sensor 126 here is fastened to the shell 16 in register with a channel 96, with the distal end of the sensor 126 emerging into that channel 96, without actually having to touch the fluid (not shown). Such a pressure sensor measures the pressure via the outer surface of the bag 10.

It should furthermore be noted that the shell 16 also comprises, installed behind that shell 16, a female connector (not shown) enabling power to be supplied to the valves, the sensors 126, the distributor and the verification and control unit, which are integrated into that shell 16. The supply (for power and control) is thus electrical and pneumatic. A male connector (not shown) arranged on the base 2 of the device 1 can be connected to the female connector of the circuit 8.

The bag 10 comprises two flexible films 65 and 66 (FIG. 2) connected to each other by a seal delimiting a closed contour, and the connectors 11 of the conveying network 12.

Here, each of the films 65 and 66 is a PureFlex™ film from the applicant. This is a co-extruded film comprising four layers, respectively, from the inside to the outside, a layer of ultra low density polyethylene (ULDPE) forming the material for contact with a liquid, a copolymer of ethylene and vinyl alcohol (EVOH) forming a barrier to gases, a copolymer layer of ethylene and vinyl acetate (EVA) and a layer of ultra low density polyethylene (ULDPE) forming the outer layers.

The seal is a weld bead formed at the periphery of the films 65 and 66 at the location of the conduits 13.

The closed contour of the bag 10 forms the liquid treatment zone 67, in which extend the conduits 13.

The closed contour has a first side 68, a second side 69 that is an opposite side to the first 68, a third side 70 meeting the first and second sides 68 and 69 and a fourth side 71 that is an opposite side to the third side 70 and that meets the first and second sides 68 and 69. The connectors 11 of the conveying network 12 emerge inside and outside the first, second, and third sides 68, 69, and 70, as can be seen more particularly in FIG. 7.

The dimensions of the bag 10 correspond to those of the surfaces of the shells 16 and 17.

The bag 10 is provided to be clamped between by the shells 16 and 17 with a major part of one of the faces of the bag 10 in contact with the face of the shell 16, and with a major part of the other face of the bag 10 being in contact with the face of the shell 17.

At its fourth side 71, the bag 10 further comprises the two through apertures 73 for positioning which were referred to above.

These positioning apertures 73 are aligned and evenly spaced apart and serve for the positioning of the bag 10 on the shell 16.

The bag 10 further comprises, in its treatment zone, the four through apertures 75 referred to above for locking the shells 16 and 17 together, these locking apertures 75 having a greater diameter than the positioning apertures 73.

These locking apertures 75 are situated in the treatment zone 67 at the locations where there are the most conduits 13, since it is at these locations where the force of pressure is greatest during the treatment. The locking apertures 75 are thus at least partially surrounded by conduits 13.

The bag 10 further comprises two other positioning apertures 77 referred to above which serve for the positioning of the door 20 in the closed door position of the device.

One of the positioning apertures 77 is situated at the fourth side 71 of the bag 10 in the vicinity of the positioning aperture 73 situated at the top left of the bag 10, and the other positioning aperture 77 is situated at the opposite extreme, that is to say towards the bottom of the bag 10, in the treatment zone.

The bag 10 further comprises, in its treatment zone 67, a plurality of portions 175 (without holes), one of which can be seen in FIG. 2, which are more than clamped by the shells 16 and 17 since the parts of the films 65 and 66 forming those portions 175 are jammed, even tangled, between the jamming nipples 173 and the jamming channels 174.

As is clearly visible in FIG. 2, the straight wall 181 of a nipple 173 is received against the back wall 191 of the channel 174, the straight longitudinal walls 193 of the channel 174 face the straight longitudinal walls 183 of the nipples 173, the beveled longitudinal walls 182 of the nipples 173 are received bearing against the beveled longitudinal walls 192 of the channel 174, and the front wall 178 of the male insert 171 is received bearing against the straight walls 194 of the female insert 172.

The jamming nipple 173 is thus fitted into the jamming channel 174, in which the films 65 and 66 of the portion 175 in the treatment zone 67 of the bag 17 are jammed to enable the bag 10 to be positioned and fixed in position prior to the treatment of the biological liquid and in order for the bag 10 to securely maintain its position during the treatment.

FIGS. 13, 15, 17 and 19 illustrate variant embodiments of the male insert 171 of FIGS. 5 to 8, while FIGS. 14, 16, 18 and 20 illustrate variant embodiments of the female insert 172 of FIGS. 9 to 12.

The male inserts 171 of the respective FIGS. 13, 15, 17 and 19 are configured to form, with the female inserts 172 of the respective FIGS. 14, 16, 18 and 20, jamming systems that are distinct from each other.

The same references have been used here for the male and female inserts of FIGS. 13 to 20 as for the male and female inserts of FIGS. 5 to 12 since only a few design details change between those inserts.

Figure 13:
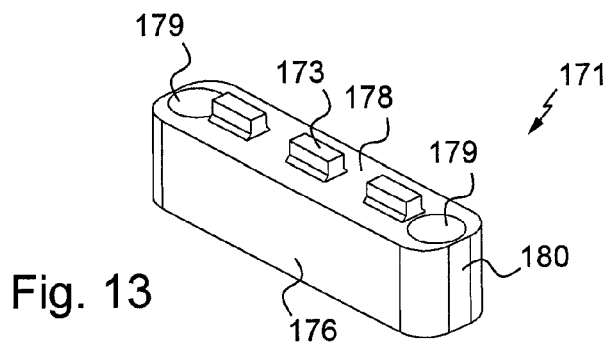
FIGS. 13 to 20 are perspective views showing variant embodiments of the jamming member and of the complementary jamming member illustrated respectively in FIGS. 5 to 8 and 9 to 12.
Figure 14:
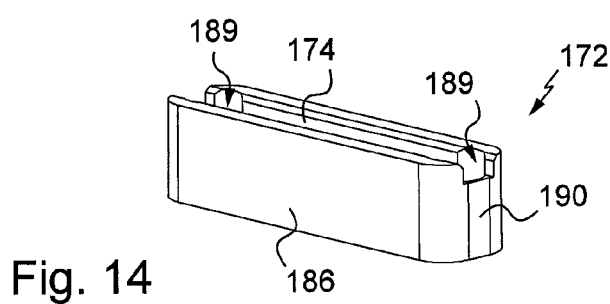

The male insert 171 of FIG. 13 is smaller than the male insert of FIGS. 5 to 8 and is only provided with three jamming nipples 173 which are similar and regularly distributed; and the corresponding female insert 172 (FIG. 14) is of a size adapted to that male insert 171 with a single jamming channel 174 of adapted size.

Figure 15:
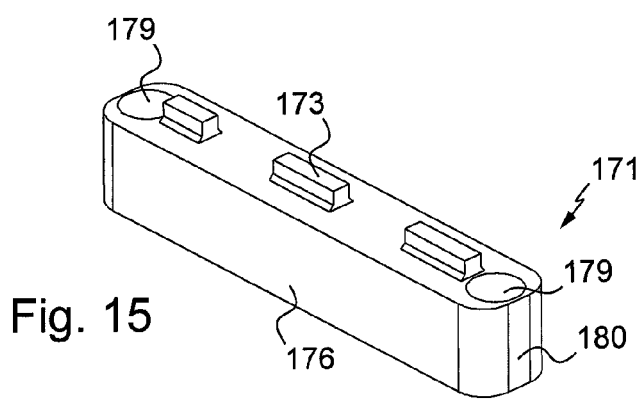
Figure 16:
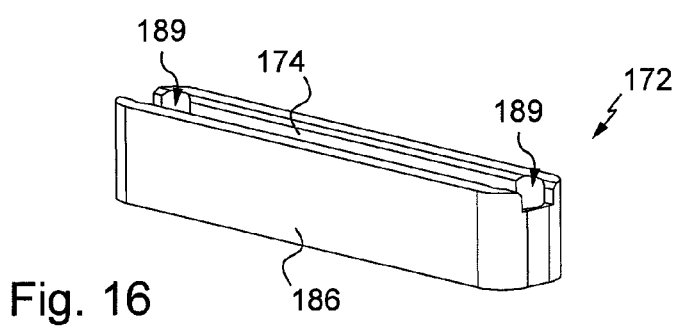

The male insert 171 of FIG. 15 is also smaller than the male insert of FIGS. 5 to 8 but larger than that of FIG. 13, while it is also provided with three jamming nipples 173 which are distinct here (one of them is smaller than the two others) but regularly distributed; and the corresponding female insert 172 (FIG. 16) is of a size adapted to that male insert 171 with a single jamming channel 174 of adapted size.

Figure 17:
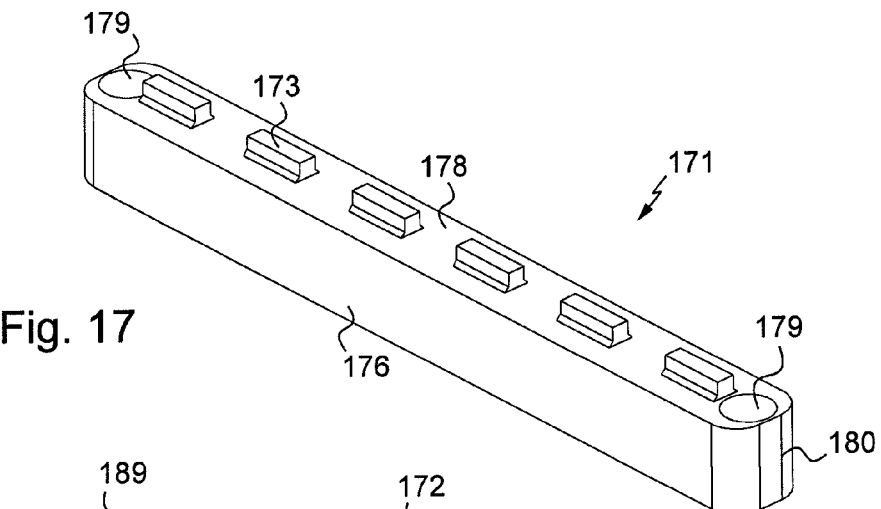
Figure 18:
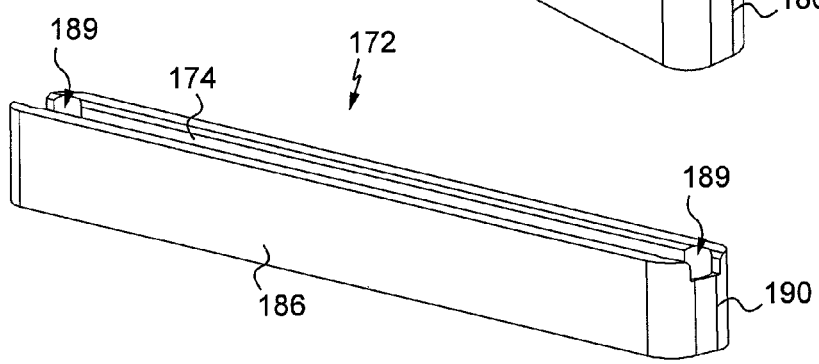
Figure 19:
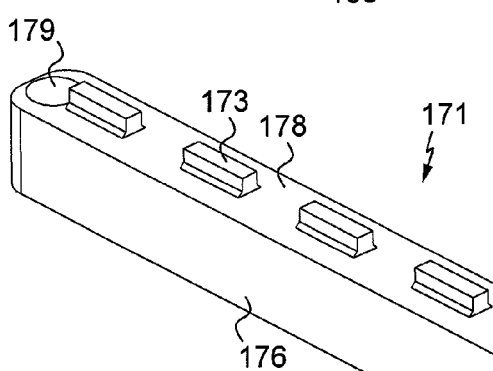
Figure 20:
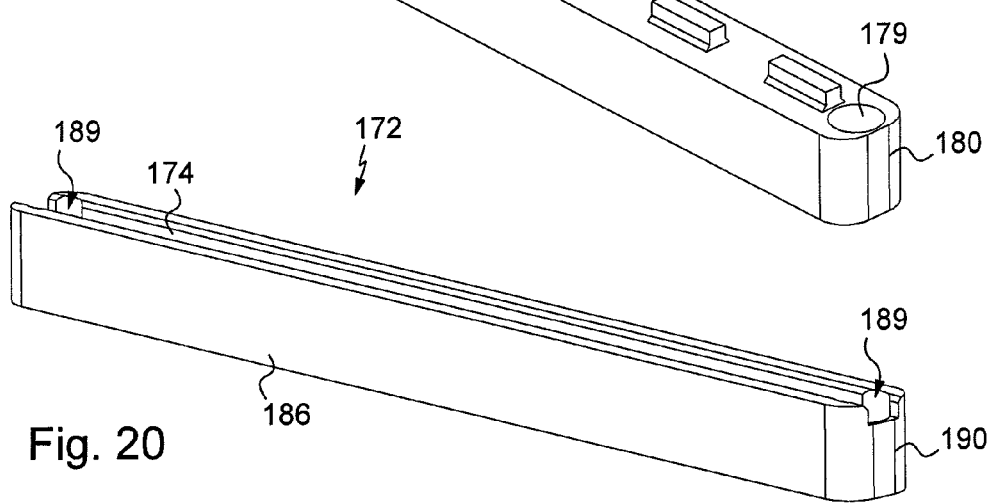

The male inserts 171 of FIGS. 17 and 19 are larger than the male insert of FIGS. 5 to 8 and are respectively provided with six and seven jamming nipples 173 which are similar and regularly distributed; and the corresponding female inserts 172 (FIGS. 18 and 20) are each of a size adapted to the respective male insert 171 with a single jamming channel 174 of adapted size.

In variants that are not illustrated:
- the male insert is not fastened to the shell in the door but to the shell on the base and the female insert is not fastened to the shell on the base but to the shell in the door;
- the male and female inserts are not fastened by screws in the shells but are instead bonded;
- the male and female inserts are implanted differently to the example of FIGS. 1, 3 and 4, there may be more or fewer of them, so long as they enable the positioning of the bag to be positioned and fixed before and during the treatment of the biological liquid;
- the jamming nipples are of slightly different form to that illustrated in the drawings, for example they do not have a flared base, or they are rounded, etc.;
- the female insert does not include a single channel formed in the main opening but instead a plurality of channels formed in that opening and which are separated from each other by the body of that female insert;
- the male and female inserts are not of parallelepiped shape but instead of cylindrical shape, for example oval or circular cylindrical;
- the male inserts may have more or fewer jamming nipples than in the drawings and the nipples may furthermore be juxtaposed, the female inserts of course being configured accordingly;
- the hinge system comprises a door having a horizontal hinging axis rather than a single hinge situated in a corner; that door having a horizontal hinging axis is fastened to the top or bottom of the front face of the base of the device; like the single hinge, that door having a horizontal hinging axis enables lateral clearances to be created over a major portion of the outline of the bag;
- the door is removable, that is to say that it is independent from the base, and it is mounted on the base for its fastening thereto;
- the ball-lock pins are of single-acting type, or are electrical or hydraulic, rather than pneumatic, or there is a system different from ball-lock pins, for example with hooks;
- the bag is triangular or circular rather than rectangular, and the case arising the shells are adapted to the shape of the bag, as well as, if desired, the door and the base; for example, in the case of a triangular bag, the door has only three sides and the hinge system is configured such that it forms lateral clearances at least at the location of the remaining two sides;
- instead of being in one piece, the shells are formed by a set of modular members associated with each other to delimit the different portions of the circuit, which members are provided with marks or labels to ensure that they are correctly disposed relative to each other. The marks and the labels comprise for example reference numbers or codes and may be of the RFID type;
- the shells are of a material other than polyoxymethylene, for example stainless steel, or aluminum, or of another plastics material in particular having a high density, or of ceramic or wood;
- the shell 16 only comprises two hooking studs 106, or more than three, and, the case arising, the bag 10 comprises respectively only two or more than three positioning apertures 73, and for the shell 17 only comprises two or more than three positioning holes 86, those studs, apertures and holes being evenly spaced, or not;
- the shell 16 comprises more than two positioning dowel pins 107 and the case arising, the bag 10 comprises more than two positioning apertures 77, and the shell 17 comprises more than two positioning holes 87, those studs, apertures and holes being evenly spaced, or not;
- the shell 16 comprises more than two locking holes 108 and the case arising, the bag 10 comprises more than two locking apertures 75, and the shell 17 comprises more than two locking holes 88;
- the films of the bags are of a material other than the Pure-Flex™ film, for example of another film with several layers compatible with biological liquids such as the film HyQ® CX5-14 available from the company Hyclone industries, or the film Platinum UltraPac available from the company Lonza; and/or
- the shaping channels are of circular section rather than semi-elliptical cross-section.

It should be noted more generally that the invention is not limited to the examples described and represented.

The invention claimed is:

1. A device for a biological liquid treatment installation, comprising a base having a front face, and a circuit comprising a plurality of connectors and a network for conveying liquid between said connectors, which circuit comprises a bag comprising two flexible films and said conveying network connectors, which circuit further comprises a press comprising a first shell disposed upright on said front face of said base and a second shell mounted on said first shell, said first shell and second shell cooperating with said bag to form, between said flexible films, by clamping of said bag between said first shell and said second shell, conduits of said conveying network; the two said flexible films of said bag being joined to each other and delimiting a treatment zone for said liquid according to a closed outline, said conveying network connectors emerging on the inside and on the outside of at least one side of said outline;
wherein said press is provided with a system for jamming said bag at the location of said treatment zone thereof, said jamming system comprising at least one jamming member for jamming said bag and at least one complementary jamming member for jamming said bag, said at least one jamming member being provided with at least one jamming nipple and said at least one complementary jamming member being provided with at least one jamming channel configured to receive said at least one jamming nipple; said at least one jamming member, said at least one complementary jamming member and said bag being configured in order for the latter to have at least one portion in said treatment zone in which said films are jammed between said at least one jamming nipple and said at least one jamming channel.

2. A device according to claim 1, wherein said at least one jamming member is fastened in a first recessed accommodation of said first shell and said at least one complementary jamming member is fastened in a second recessed accommodation of said second shell.

3. A device according to claim 2, wherein said at least one jamming member and said at least one complementary jamming member are disposed facing said treatment zone and in immediate proximity to a plurality of conduits of said routing network.

4. A device according to claim 2, wherein said at least one jamming member and said at least one complementary jamming member are each disposed in a similar position to that of said first shell on said front face of said base.

5. A device according to claim 2, wherein said at least one jamming member is provided with a plurality of jamming nipples distributed longitudinally, regularly or irregularly, on a front wall of said at least one jamming member.

6. A device according to claim 2, wherein said at least one complementary jamming member is provided with a single jamming channel formed longitudinally in a main opening of said at least one complementary jamming member.

7. A device according to claim 2, wherein said bag comprises first through apertures on one side of said bag for its positioning, and said first shell comprises studs for hooking said bag to an upper part of said first shell, said hooking studs being configured to pass through said first through apertures of said bag .

8. A device according to claim 2, wherein said second shell has a first hole, said bag comprises at least one second through aperture in said treatment zone and said device comprises a press locking system configured such that it locks said first shell and second shell together, which system is provided with at least one ball-lock pin having an unlocked state and a locked state, said ball-lock pin being fastened to said first shell, being configured to pass through said first shell and said second through aperture and to emerge in said first hole of said second shell, where said ball-lock pin is furthermore configured to be free therein in said unlocked state and to be fastened therein in said locked state.

9. A device according to claim 2, wherein said bag comprises at least one third through aperture on one side of said bag, said first shell comprises at least one dowel pin configured to pass through said third through aperture, and said second shell comprises at least one second hole configured to receive said dowel pin of said first shell.

10. A device according to claim 2, further comprising a movable or removable door, said device having a closed door position, in which second shell is disposed in said door to form said circuit and which furthermore has a position other than said closed door position, in which said bag is carried only by the first shell.

11. A device according to claim 10, further comprising a hinge system hinging said door relative to said base, said hinge system being disposed only on one side of said door so as to form, in the closed door position, lateral clearances between said door and said base over the rest of a perimeter of said door, so as to enable free access to the connectors of said bag.

12. A device according to claim 2, wherein said circuit comprises instruments necessary for the treatment of said biological liquid, said instruments selected from the group consisting of valves to allow or prevent the passage of said liquid in said conduits, and sensors of physico-chemical values of said liquid, and wherein said instruments are integrated into said first shell.

13. A device according to claim 4, wherein said at least one jamming member and said at least one complementary jamming member are each disposed in a substantially vertical, or in a position perpendicular to that of said first shell on said front face, or in an intermediate inclined position.

14. A device according to claim 1, wherein said at least one jamming member is of parallelepiped general shape provided with a front wall from which projects said at least one jamming nipple.

15. A device according to claim 14, wherein said at least one complementary jamming member is of parallelepiped general shape provided with a main opening in which is provided said at least one jamming channel.

16. A device according to claim 15, wherein said at least one jamming nipple has a flared base and a straight wall remote from said flared base, and said at least one jamming channel has a back wall and flared edges.

17. A device according to claim 1, wherein said at least one jamming member and said at least one complementary jamming member are disposed facing said treatment zone and in immediate proximity to a plurality of conduits of said routing network.

18. A device according to claim 1, wherein said at least one jamming member and said at least one complementary jamming member are each disposed in a similar position to that of said first shell on said front face of said base.

19. A device according to claim 18, wherein said at least one jamming member and said at least one complementary jamming member are each disposed in a substantially vertical, or in a position perpendicular to that of said first shell on said front face, or in an intermediate inclined position.

20. A device according to claim 1, wherein said at least one jamming member is provided with a plurality of jamming nipples distributed longitudinally, regularly or irregularly, on a front wall of said at least one jamming member.

21. A device according to claim 1, wherein said at least one complementary jamming member is provided with a single jamming channel formed longitudinally in a main opening of said at least one complementary jamming member.

22. A device according to claim 1, wherein said bag comprises first through apertures on one side of said bag for its positioning, and said first shell comprises studs for hooking said bag to an upper part of said first shell, said hooking studs being configured to pass through said first through apertures of said bag.

23. A device according to claim 1, wherein said second shell has a first hole, said bag comprises at least one second through aperture in said treatment zone and said device comprises a press locking system configured such that it locks said first shell and second shell together, which system is provided with at least one ball-lock pin having an unlocked state and a locked state, said ball-lock pin being fastened to said first shell, being configured to pass through said first shell and said second through aperture and to emerge in said first hole of said second shell where said ball-lock pin is furthermore configured to be free therein in said unlocked state and to be fastened therein in said locked state.

24. A device according to claim 1, wherein said bag comprises at least one third through aperture on one side of said bag, said first shell comprises at least one dowel pin configured to pass through said third through aperture, and said second shell comprises at least one second hole configured to receive said dowel pin of said first shell.

25. A device according to claim 1, further comprising a movable or removable door, said device having a closed door position, in which second shell is disposed in said door to form said circuit and which furthermore has a position other than said closed door position, in which said bag is carried only by the first shell.

26. A device according to claim 25, further comprising a hinge system hinging said door relative to said base, said hinge system being disposed only on one side of said door so as to form, in the closed door position, lateral clearances between said door and said base over the rest of a perimeter of said door that does not include said one side of said door, so as to enable free access to the connectors of said bag.

27. A device according to claim 1, wherein said circuit comprises instruments necessary for the treatment of said biological liquid, said instruments selected from the group consisting of valves to allow or prevent the passage of said liquid in said conduits, and sensors of physico-chemical values of said liquid, and wherein said instruments are integrated into said first shell.

28. A device according to claim 2, wherein said at least one jamming member is of parallelepiped general shape provided with a front wall from which projects said at least one jamming nipple.

29. A device according to claim 28, wherein said at least one complementary jamming member is of parallelepiped general shape provided with a main opening in which is provided said at least one jamming channel.

30. A device according to claim 29, wherein said at least one jamming nipple has a flared base and a straight wall remote from said flared base, and said at least one jamming channel has a back wall and flared edges.

* * * * *